United States Patent [19]
Fairlie et al.

[11] Patent Number: 5,087,822
[45] Date of Patent: Feb. 11, 1992

[54] ILLUMINATION SYSTEM WITH INCIDENT BEAMS FROM NEAR AND FAR DARK FIELD FOR HIGH SPEED SURFACE INSPECTION OF ROLLED ALUMINUM SHEET

[75] Inventors: Matthew Fairlie; David Smith; Warren Fraser, all of Kingston, Canada; Otto Meijer, Fulton, N.Y.

[73] Assignee: Alcan International Limited, Montreal, Canada

[21] Appl. No.: 701,306

[22] Filed: May 13, 1991

Related U.S. Application Data

[63] Continuation of Ser. No. 543,202, Jun. 22, 1990, abandoned.

[51] Int. Cl.$^5$ .............................................. G01N 21/88
[52] U.S. Cl. .................................. 250/572; 356/446
[58] Field of Search ............... 250/571, 572; 356/445, 356/446, 448, 371

[56] References Cited

U.S. PATENT DOCUMENTS

| | | | |
|---|---|---|---|
| 3,892,492 | 7/1975 | Eichenberger | 250/571 |
| 4,539,561 | 9/1985 | Wulff | 340/675 |
| 4,595,289 | 6/1986 | Feldman et al. | 250/572 |
| 4,629,319 | 12/1986 | Clarke et al. | 356/237 |
| 4,675,730 | 6/1987 | Asomaitis et al. | 358/106 |
| 4,806,776 | 2/1989 | Kley | 250/560 |
| 4,863,268 | 9/1989 | Clarke et al. | 356/237 |

OTHER PUBLICATIONS

Otto Meijer and Doug Keim, Design and Performance of a High Speed Surface Inspection System From Aluminum Strip, IEEE Conference at San Diego (1989).

Primary Examiner—David C. Nelms
Assistant Examiner—Que T. Le
Attorney, Agent, or Firm—Cooper & Dunham

[57] ABSTRACT

Apparatus and method for inspecting surface quality of a moving sheet of metal illuminates a surface of the moving sheet by the use of at least two lamps. The region which is illuminated by the lamps is inspected by a sensing device. The angle of incidence for the light beams from the lamps are from the near and dark fields. The sensing device picks up highlighted or brightened portions of the sheet due to surface irregularities. By use of a multiplicity of lamps and a single sensing device, such as a video recorder, an inexpensive yet very sensitive system is provided for detecting irregularities in the surface of the moving sheet. The system may be observed by an operator to determine locations of irregularities and as well the system may be adapted to document locations on the moving sheet where the irregularities occur.

19 Claims, 3 Drawing Sheets

ILLUMINATION SYSTEM WITH INCIDENT BEAMS FROM NEAR AND FAR DARK FIELD FOR HIGH SPEED SURFACE INSPECTION OF ROLLED ALUMINUM SHEET

This is a continuation of application Ser. No. 543,202, filed June 22, 1990, abandoned on 7/2/91.

FIELD OF THE INVENTION

This invention relates to method and apparatus for inspecting surface quality of a moving sheet of metal.

BACKGROUND OF THE INVENTION

There are a variety of applications for inspecting surface quality of manufactured products. The ultimate quality of the surface not only determines marketability of the product, but finish durability as well. A variety of systems have been developed to inspect a multiplicity of surfaces, such as painted panels in the automotive field, appliance, furniture and aircraft fields, the inspection of painted rolled sheet and high speed steel and aluminum sheet. A variety of applications of these products demand superior surface finish. Until the advent of machine vision, products were inspected by human inspectors. Out of necessity, this inspection was carried out at low line speeds to prevent blurring to the eye.

A variety of electronic devices have been developed which are either operator dependent or completely automated to detect surface finish imperfections and either signal or document such imperfections. This permits various types of assembly lines and manufacturing lines to operate at normal processing speeds.

A system which interfaces with the operator is disclosed in U.S. Pat. No. 4,539,561. The system is adapted to detect surface quality of cast aluminum strip. At least one video camera is used in the detection process. The system is adapted to restrict transmission from the camera to the TV monitor, so that only defective sections of the cast aluminum strip are shown on the TV camera. This considerably reduces the time that the operator must concentrate on the TV camera to detect surface imperfections and hence provides a more acute attention span for areas of the cast aluminum strip where surface imperfections are detected by the system. The signal from the video camera is delimited with an upper and lower signal strength Defective surface conditions cause the signal from the video camera to exceed or fall below these limits. At that point, recording and transmission of the image to the TV monitor is triggered. The operator can then view the imperfection and decide on a course of action to deal with the imperfection in the cast strip.

U.S. Pat. No. 4,863,268 discloses a surface detection system which is particularly useful in detecting irregularities or flaws in the surface of automobile panels. The source of light and camera are both oriented in the same direction. A reflective surface is used to direct light reflected from the surface being inspected back to the camera. By rereflecting the light over the surface being inspected, a shadow may be produced as observed by the camera which is indicative of the quality of the surface finish. Although the system is compact, it provides, however, for only a single light source and a single camera which limits the types of surface imperfections which can be detected. As such the system is not particularly useful in detecting surface imperfections on high speed conveyed sheet material.

A similar system is disclosed in U.S. Pat. No. 4,629,319 involving a single TV camera and a single light source. Both the light source and camera may be mounted on robotic arms. The light source may be altered with a grill to provide a plurality of light lines all of the same intensity. By virtue of mounting the lamp and camera on separate robotic arms, their angular position may be varied as the system traverses the surface being inspected to enhance the highlighting of the surface imperfections. The system is particularly useful at low angles to detect surface imperfections, such as poorly oiled panels. However, this greatly expands the size of the system. Therefore it is desired to inspect the panel with an angle of incidence for the light beam of greater than 50° relative to the planar surface of the sheet or panel being inspected. In order to operate at these higher angles, manipulation of the robotic arms and, in turn, varying the position of the lamps and camera are required to detect surface imperfections. Although the system is effective in detecting surface imperfections on the order of mm in section on complex car panel shapes which are generally smooth surfaces, it is a relatively expensive system to install.

U.S. Pat. No. 4,675,830 discloses a video surface inspection system particularly adapted to sense imperfections in high speed aluminum sheet. The system is capable of detecting surface imperfections in sheet moving at speeds up to 3600 feet per minute. The system employs a plurality of lamps which direct light beams transversely of the motion of the sheet. Two light sources positioned on opposite sides of the sheet provide diffuse lighting while two other lamps positioned above and to each side of the sheet provide specular lighting. With the lamps positioned to each side of the sheet and transversely lighting the sheet, a plurality of video cameras are positioned above the sheet to detect highlighted surface irregularities in the moving sheet. The system is devised to provide diffused and/or specular illumination which gives a more homogeneous coverage of the web surface where it is thought that a combination of diffuse and specular illumination can be used to highlight variations in the surface being examined. It is preferred that the lamps emit a longwave invisible (red) portion of the spectrum to match the image sensors of the video cameras and as well to improve the work environment.

SUMMARY OF THE INVENTION

According to an aspect of the invention, an apparatus is provided for inspecting surface quality of a moving sheet of metal. The apparatus comprises:

means for supporting the apparatus in a stationary position relative to a moving sheet of metal to be inspected;

means for illuminating a surface of a moving sheet of metal to be inspected with at least two incident beams of light;

means for inspecting the illuminated surface to detect intensity differences in light reflected by the illuminated surface from the at least two incident beams of light;

the illuminating means is mounted on the support means for directing the at least two incident beams of light in a direction along the moving sheet of metal and the inspecting means being mounted on the support means to receive the reflected light;

the illuminating means comprises at least two lamps each of which is adapted to emit a respective beam of light where each beam is elongate and narrow in cross-section and of a width at least as wide as a moving sheet of metal to be inspected;

each of the at least two lamps is positioned on the support means to direct its corresponding beam of light onto an inspection region through which the sheet of metal moves. Each beam emitted from the respective lamp is at a different angle of incidence relative to the other beams of light. This provides at least two corresponding incident beams from a near dark field and a far dark field;

means for controlling beam intensity of each of the lamps to permit independent adjustment of beam intensity of each of the at least two lamps;

the inspecting means comprises means for sensing light reflected by a surface irregularity from at least one of the near dark field and the far dark field relative to the inspection region;

the sensing means senses reflected light simultaneously from the at least two lamps while remaining at a single angle of reflection relative to normal for the inspection region;

means detects sensed reflected light from the inspection region which is of an increased intensity greater than a predetermined minimum intensity or less than a predetermined maximum The detected reflected light of increased intensity, or decreased intensity, is indicative of an irregularity in surface quality of the moving sheet of metal; and means for recording location on the moving sheet of metal of a detected irregularity in surface finish quality.

According to another aspect of the invention, a method is provided for inspecting surface finish quality of a moving sheet of metal. The methods comprises:

moving the sheet of metal through an inspection region;

illuminating a surface of the sheet of metal to be inspected with at least two incident beams of light from at least two corresponding lamps;

orienting the lamps to direct the at least two beams of light having a plane of incidence along the direction of sheet motion;

adapting each of the at least two lamps to emit a respective beam of light which is elongate and narrow in cross-section;

positioning each of the at least two lamps to direct the at least two beams of light onto the inspection region at a different angle of incidence relative to each other to provide at least two corresponding incident beams from a near dark field and a far dark field;

controlling beam intensity of each of the at least two lamps to permit independent adjustment of beam intensity of each of the at least two lamps;

sensing simultaneously light reflected by a surface irregularity from incident light of the near dark field and the far dark field. The sensing of light is conducted at a single angle of reflection which in turn determines the near dark field and the far dark field for the incident beams of light;

detecting sensed reflected light from the inspection region which is of a increased intensity greater than a predetermined maximum intensity or of a decreased intensity less than a predetermined minimum intensity. The predetermined maximum or minimum intensity is set so that reflected light of increased or decreased intensity indicates an irregularity in surface quality; and recording location on the moving sheet of metal of the detected irregularity in surface quality.

BRIEF DESCRIPTION OF THE DRAWINGS

Preferred embodiments are described herein with reference to the drawings wherein.

DETAILED DESCRIPTION OF THE PREFERRED EMBODIMENTS

Figure 1A:
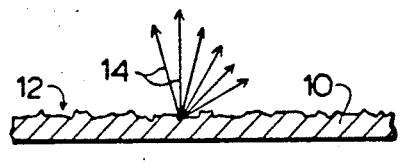
FIGS. 1a and 1b schematically demonstrates types of light scattering.

The system, according to this invention, is capable of detecting a variety of defects in the object surface where the size of such defects may be in the range of 20 $\mu$m. Furthermore, the surface being inspected may be relatively rough as compared to the smooth surfaces of the car panels. According to an aspect of this invention, the system is particularly useful in simultaneously detecting the following three types of defects:

1. Type A Defect—defect which scatters light diffusely or at angles far from the specular direction. For example, chatter cinch marks in the sheet reflect light this way.
2. Type B Defect—defect which reflects light strongly in a direction close to the specular direction. For example, roll marks in the sheet reflect light in this manner.
3. Type C Defect—defect which absorbs light and reduces reflected light intensity at the detector. For example, holes in the sheet reduce reflected light intensity in this way.

With reference to FIG. 1 of the drawings, types A and B defects are shown. The sheet of material 10 has a roughened surface 12 of several irregularities. Incident light onto the surface 12 is then reflected in a diffuse manner as indicated in region 14. Different from this is a sheet 16 having roll marks which are planar to some extent so that incident light onto the surface 18, where the defect occurs at 20, provides reflected light which is reflected very closely to the specular direction as indicated at 22. In accordance with this invention, the use of at least two lamps positioned in the near and far dark fields, in combination with a single line scan sensing device which may be a video camera or the like, permits the simultaneous detection of the above-noted types A, B and C defects in accordance with the manner discussed with respect to details of the apparatus and method of FIGS. 4 and 5.

Figure 2:
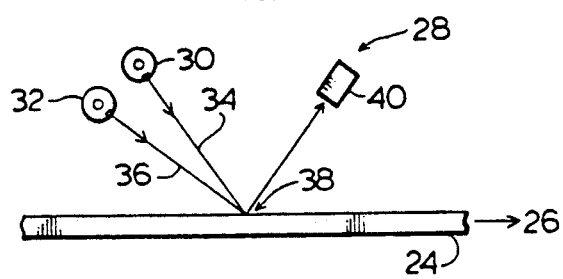
FIG. 2 schematically shows the relative arrangement of the illumination and sensing devices of the apparatus according to this invention.

To accomplish this simultaneous detection of types A, B and C defects and other similar defects, the apparatus is based on the light and sensing arrangement of FIG. 2. The sheet of material 24 is conveyed in the direction of arrow 26 beneath the stationary apparatus generally designated 28. As will be discussed in more detail with reference to FIG. 4, the mounting of the components of the apparatus 28 is described. For purposes of the schematical representation of FIG. 2, the lamps 30 and 32 project or emit respective beams of light 34 and 36 towards the sheet 24. The lamps 30 and 32 are adapted to emit beams of light 34 and 36 which are of a width at least the width of the sheet 24 and of narrow elongate cross-section. The beams are focused onto the same region, generally indicated 38, which for purposes of discussion with this apparatus is defined as the inspection region. Hence the sheet 26 is conveyed or passed or moved through the inspection region 38. The light energy from lamps 30 and 32 is projected continuously onto the inspection region 38.

Figure 1B:
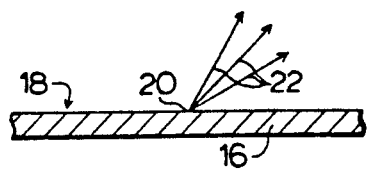

In accordance with the principles set forth in FIGS. 1a and 1b, depending upon the type of defect the light is reflected from the surface of sheet 24 in either a diffuse or close to specular direction, the sensing device 40, which in accordance with this embodiment is a line scan video camera, electronically senses the light intensity reflected from the inspection region 38. In order to further understand the positioning of lamps 30 and 32 and for future reference in the specification, the lamps are positioned in the near dark field and the far dark field. These positions are defined with reference to the metal surface such as rolled aluminum surfaces where light reflected within 5° of the specular direction, but not along the specular direction, is taken to mean light reflected from the near dark field The far dark field refers to scattered light directions greater than 5° from the specular direction. Due to the positioning of the lamps 30 and 32 in the near dark field and in the far dark field respectively, light reflected from an irregularity on the surface 24 which is received by the camera 40 is of a higher or lower intensity. It is only the surface irregularities which cause an increase or decrease in reflected light intensity in the direction of the receiving area of the camera 40. Hence the light from the near dark field and from the far dark field highlight surface irregularities of the sheet 24 as it is passed in the direction of arrow 26 through the inspection region 38. By virtue of use of at least lamps in the near and far dark fields, both type A and type B defects of FIGS. 1a and 1b are highlighted and received simultaneously by the camera 40. Type C defects are detected as reduction in light intensity reflected by the surface illuminated by the near dark field lamps. The electronic information, as gathered by the video camera 40, is then processed in accordance with the system identified in FIG. 5.

Although preferred aspects of the invention are discussed with respect to inspecting surface quality of aluminum sheet, it is understood that the principles of the invention, as exemplified in the preferred embodiments, may be applied to surface quality detection of other types of sheet, panel and the like materials. The significant feature of this system is that light scattered by mechanical damage in the sheet surface or the lack of light associated with changes in optical reflectivity due to discoloring or darkening of the surface can be detected simultaneously. For purposes of aluminum sheet inspection, the system may be adapted to take into account oil residues which change the reflectivity of the sheet surface. Oil residues are not considered to be defects in most aluminum sheets. The optical system of this invention is then adaptable to detect defects which are caused by mechanical roughness, but insensitive to surface reflectivity changes due to oil residues This is accomplished by the use of a single camera in conjunction with at least two lamps, two of which are positioned in the near dark field and the far dark field. This permits the detection of surface defects as bright objects while defects associated with reduced reflectivity, such as oil residues, appear as low contrast objects. In the far dark field, the reduction in reflectivity associated with oil residues is relatively small. Hence oil residues can be distinguished by electronic threshholding, from "dark" or "light" defects using this type of multiple lighting system; whereas Type C defects can be still detected because of significantly reduced reflectivity in both far and near dark fields The system is designed to detect Type C defects by determining that reflectivity is reduced below a predetermined minimum level for both far and near dark fields.

For type B defects, the highest contrast is achieved by positioning the light source and detector in the near dark field position with the plane of incidence along the rolling direction. For type A defects, the highest contrast is obtained with the detector and light source in a far dark field configuration. With the at least two light sources of this invention, both types of defects causing a respective style of light scattering can be detected simultaneously. Both light sources are positioned so that the sheet passes through the plane of incidence of the light sources. This orientation is preferred over having the plane of incidence directed transversely of the rolling direction because the contrast of defects is more uniform across the field of view of the camera with the orientation of the light beams according to this invention and it fits the line scan camera concept.

Figure 3:
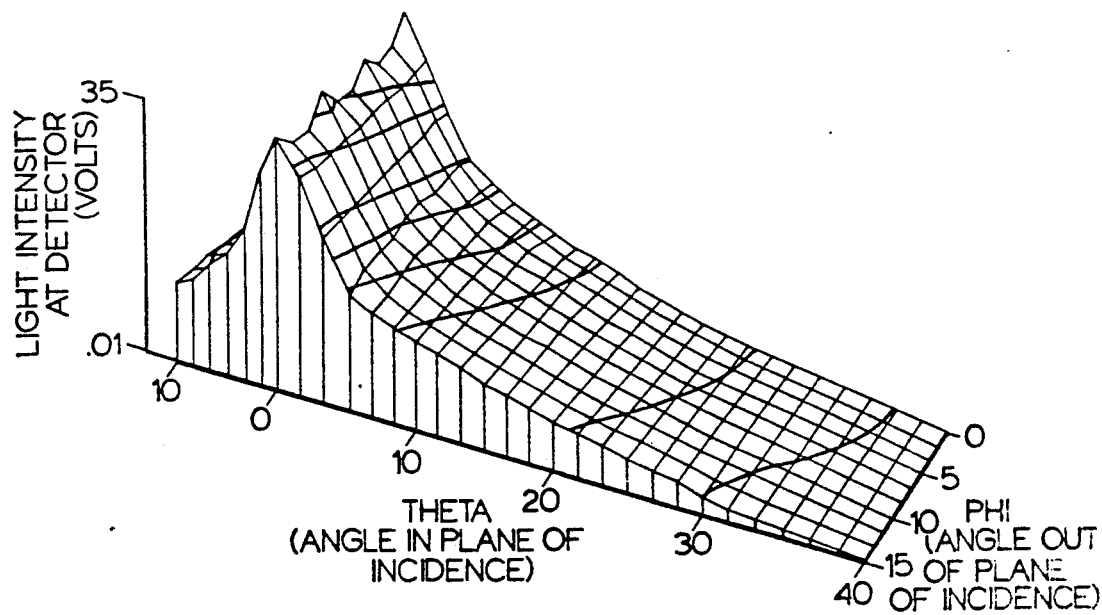
FIG. 3 is a plot showing variation in light scattering from rolled sheet depending upon angle of incidence and angle out of plane incidence for the sensing device.

FIG. 3 shows the light scattering properties of a rolled sheet of aluminum where, as with FIG. 2, the sheet is passed through the plane of incidence of the light beam. The light intensity is highest for a zero angle in the plane of incidence and a zero angle out of the plane of incidence Falling off from this highest intensity, the intensity reduces in a forward sloping direction as the angle and the plane of incidence increases and the angle out of the plane of incidence also increases. It has been found that the intensity of the light source 32 in the far dark field must be much higher than the intensity of the light emitted from the lamp 30 in the near dark field to give high contrast defects. In accordance with another aspect of this invention, due to the separate lamps a suitable control function may be employed to adjust the intensity of lamp 30 relative to the intensity of lamp 32 to enhance the electronic detection of defects in the surface.

Figure 4:
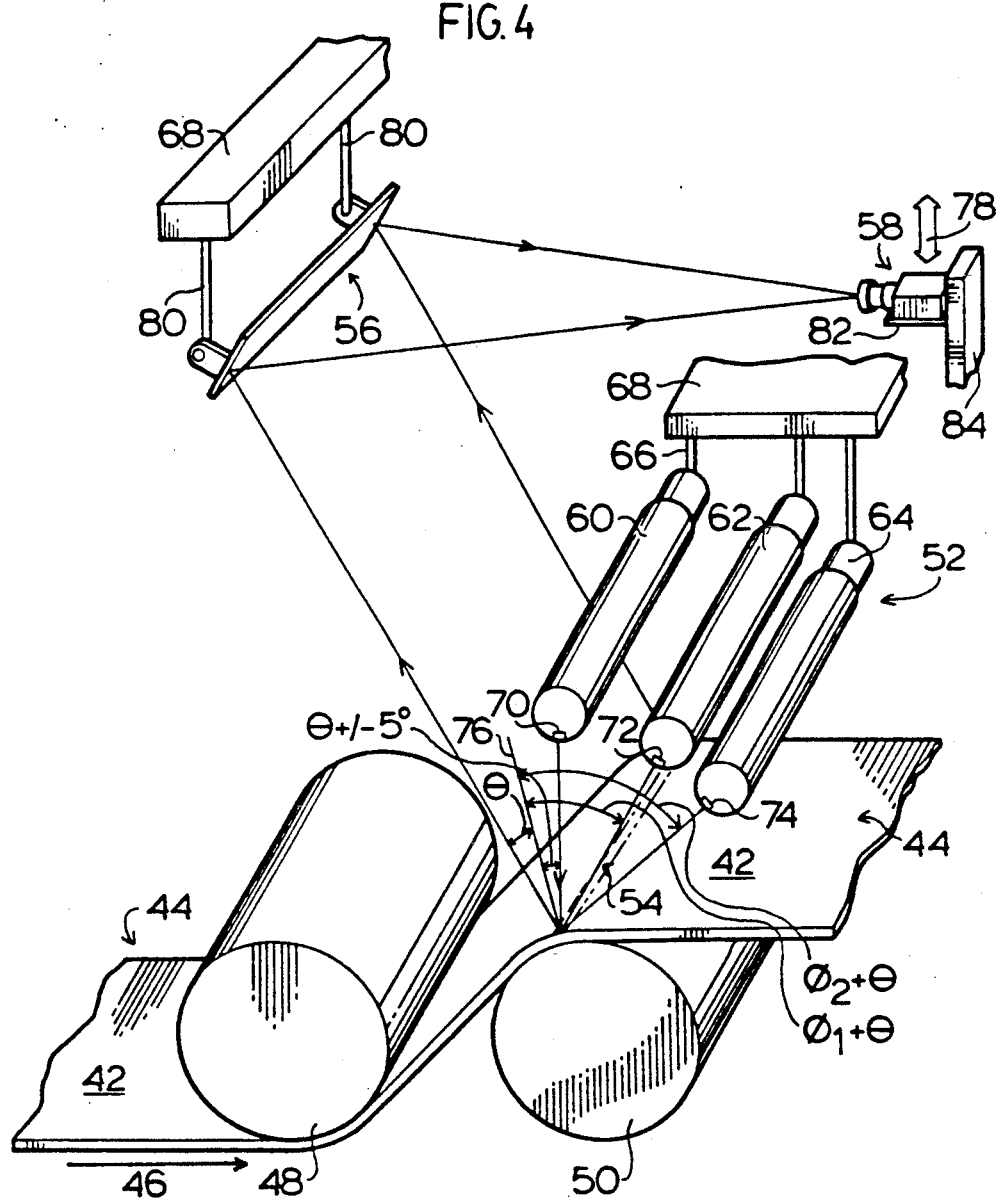
FIG. 4 is a perspective view of the surface inspecting apparatus according to a preferred embodiment of this invention.

The preferred embodiment of FIG. 4 is arranged to detect the surface characteristics of the upper surface 42 of the sheet 44 moving in the direction of 46. The sheet 44 is passed beneath roller 48 and then upwardly over 50. In accordance with this invention, an illuminating system 52 is provided to illuminate the upper surface 42 of the moving sheet 44. The illuminating system is arranged to direct the individual light beams onto the inspection region which extends across the width of the sheet 44 and is generally designated 54 by virtue of the lamps emitting beams of light which extend across the width of the sheet. A narrow inspection region is defined on the curved portion of the sheet 44 as it passes over the roller 50. A similar system could be constructed to inspect the bottom surface of sheet 44 as it passes under roller 48.

To provide for a compact set-up of the system, a mirror 56 is provided to fold the reflected light to the sensing device 58 which, in accordance with this embodiment, is a line scan video camera. The components of this system are supported stationary relative to the inspection region 54. The support components may be interconnected or supported by other surrounding structure of the rolling system so that the lamps, mirror and camera are all fixed relative to each other during any phase of the operation.

The device 52 for illuminating the inspection region 54 comprises, according to this embodiment, three lamps 60, 62 and 64. Each of the lamps is supported from a suitable standard, such as at 66, which in turn is tied into a support structure 68. As noted, this support structure may be part of the strip rolling machine or other related tower equipment. Each of the lamps 60, 62 and 64 is a high output, narrow aperture, fluorescent lamp. With reference to lamp 60, the narrow aperture is indicated at 70, with lamp 62 the aperture is indicated at 72 and with lamp 64 the aperture is indicated at 74. Each lamp then emits an elongate narrow beam of a width at least as wide as the sheet 44. The lamps are positioned on support 68 so as to direct the beam of light from each lamp towards the inspection region 54 and in a direction such that the sheet 44 travels through the angle of incidence of the lamps with the sheet. In this embodiment, the angle of incidence intersects the sheet upper surface 42 to define a linear inspection region 54 which extends across the sheet 44 and through which the sheet travels The narrow slit 70, 72 and 74 of each lamp is oriented to provide an angle of incidence which is either in the near or dark field for the lamp sources relative to the angular position of the camera 58. As shown in FIG. 4, the surface normal is indicated by line 76. Relative to the inspection region, the camera 58 is at an angle $\theta$. The beam from lamp 60 is at an angle of $\theta$ plus approximately 2°, that is slightly greater than $\theta$ so as to position it in the near dark field for the inspection region 54. The two remaining lamps 62 and 64 are in the far dark field. According to this embodiment, they are positioned at a angle greater than 5° relative to the angle $\theta$. These angles are respectively $\theta +/- \phi_1$ and $\theta +/- \phi_2$. For values of $\theta - \phi_1$ or $\theta - \phi_2$, $\theta$ is usually greater than $\phi_1$ or $\phi_2$.

According to a preferred embodiment, $\theta$ is in the range of 10° to 45°. Hence lamp 60 is normally in the $+/-2°$ to 5° range about the specular direction or in the range of 5° to 50° from normal. Lamps 62 and 63 are greater than 5° from the specular direction.

From the geometry of the lighting and sensing system of FIG. 4, it is apparent then that the bright field would be defined by an incident angle of $\theta$ which is determined by the position of camera 58 It is understood, however, that camera 58 may be moved up and down as indicated by arrow 78. The purpose for moving the camera 58 is to heighten the sensitivity to various types of surface irregularities in the sheet 44. Hence the angle $\theta$ with the lamps stationary can be altered. For example, the angle can be increased thereby positioning the lamps further into the far dark field, or conversely the angle $\theta$ may be decreased thereby positioning the lamps closer to the near dark field. The light output of the lamps may be regulated by photocells so that the intensity of the far dark field lamps can be adjusted to be much higher than the intensity of near dark field lamps. The inspection region 54 of the sheet can be fixed by wrapping the sheet around the inspection roll 50. As noted for purposes of compactness of the arrangement, the optical path from the roll to the camera may be folded at the mirror 56 to fit within the system constraints The mirrors 56 may be mounted from standards 80 which in turn are connected to a support structure which may be a continuum of support structure 68.

With the facility to change the position of the camera, as indicated by arrow 78, greater sensitivity to different types of surface imperfections, may be achieved. The camera 58 is mounted on a platform 82 which in turn is set on an adjustable device 84. The adjustable device 84 may then raise and lower the platform 82 to adjust the relative position of the camera 58. By changing the viewing angle of the camera with respect to the light sources, the intensity of the near dark field light scattering can be adjusted when the lamps are replaced Hence an adjustment to lamp intensity by varying camera position can be achieved. When the desired relationship of lamp intensity is achieved, the camera position may be held to provide for continuous operation in detecting certain types of defects.

A further feature of this arrangement is that light conditions, as seen by the camera, can be changed while a coil is being inspected to tune the inspection process to certain types of defects. A change in lighting conditions is readily incorporated into a programmed inspection procedure where the camera is positioned, as will be discussed in more detail with respect to FIG. 5, such that it can be automatically cycled up and down so that the surface is inspected under alternating bright and dark fields.

Figure 5:
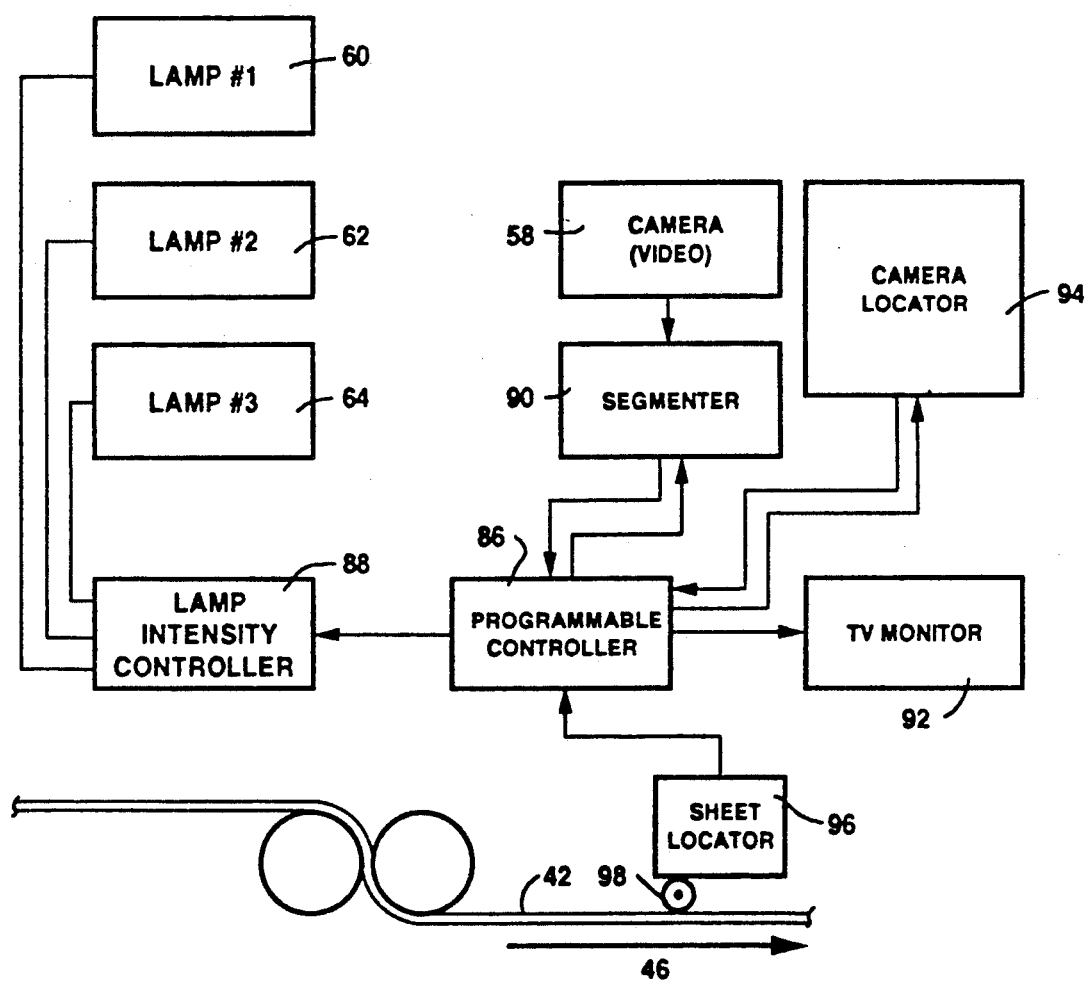
FIG. 5 is a block diagram showing components of the system controls.

The programmable aspects of the system are provided by a programmable controller 86 as shown in block in FIG. 5. The programmable controller is connected to a lamp intensity controller 88. The lamp intensity controller powers the respective lamps 60, 62 and 64. The intensity of each lamp can then be set by the lamp intensity controller 88 to achieve the desired enhancement of the surface irregularities passing through the inspection region 54. The camera 58 senses light reflected from the inspection region and transmits electronic signals representative of the light received in accordance with the standard techniques as discussed with reference to prior art patents. The signal is transferred to a segmenter 90 which establishes the predetermined minimum level of intensity Information, which indicates intensity greater or less than a preset maximum or minimum limit for reflected light levels denotes a defect and is transmitted to the programmable controller. The programmable controller then transmits to a TV monitor 92 the signal representing the surface defect in the sheet 44 in accordance with standard procedure. The operator may then view the TV monitor to determine the nature of the defect. Because of the near dark field lighting, holes will appear as dark objects with sufficient contrast to be detected by the segmenter. The defect can be detected by the signal level being less than a preset minimum.

The programmable controller can also be programmed to operate the camera locator 94 to raise and lower the camera in the direction of arrow 78 as shown in FIG. 4. This, in turn, provides better information with respect to the surface imperfections being inspected. As noted, by adjusting the camera position, the relative positions of the incident beams from the near and far dark fields are changed. For example, the lamp in the near dark field can be adjusted by the camera to be in the bright field when this happens The lamps in the far dark field are then moved towards the near dark field. Moving the camera vertically changes the viewing angle on the roll and moves the camera away from or towards the specular direction of the lamps, i.e., $\phi = 0$. To enhance the visibility of certain defects, the machine can be programmed to shift the position of the camera.

Upon locating a defect, the position on the sheet should be recorded As shown in FIG. 5, a sheet locator device 96 has a wheel 98 in contact with the sheet 44 travelling in the direction of arrow 46 to record thereby the defect position on the sheet. The sheet locator has output to the programmable controller 86 to indicate at any moment the lineal position on the sheet. The programmable controller on determining a sensed intensity of reflected light from the camera 58 may then document or record the position on the sheet by noting the lineal foot indicator output from the sheet locator 96. It is appreciated that the programmable controller may also have data output in the form of a software disc as well as hard print copy of information recorded during any one run. Furthermore, there may be electronic storage of the images received by the camera 58 so that the operator can call up on another day the type of surface imperfections in the sheet that were previously monitored.

The single camera with multiple lamp system, according to this invention, provides a very economical, accurate system for detecting a variety of surface imperfections simultaneously. The camera may be adjusted to the single angle of reflection through which reflective light is sensed from the inspection region 54. The camera angle may range from the angle $\theta$ which determines the specular direction through to an angle coincident with the near dark field which is in the range of $+/-5°$ about $\theta$ through to $\phi_2$ which may be greater than 5°. Such variation of camera position about the single angle of reflection provides for enhanced detection of various types of surface imperfections.

Although preferred embodiments of the invention have been described herein in detail, it will be understood by those skilled in the art that variations may be made thereto without departing from the spirit of the invention or the scope of the appended claims.

We claim:

1. An apparatus for inspecting surface quality of a moving sheet of metal comprising:
    means for supporting said apparatus in a stationary position relative to a moving sheet of metal to be inspected;
    means for illuminating a surface of a moving sheet of metal to be inspected with at least two incident beams of light;
    means for inspecting said illuminated surface to detect intensity differences in light reflected by such illuminated surface from such at least two incident beams of light;
    said illuminating means is mounted on said support means for directing such at least two incident beams of light in a direction along such moving sheet of metal and said inspecting means being mounted on said support means to receive such reflected light;
    said illuminating means comprises at least two lamps each of which is adapted to emit a respective beam of light where each beam is elongate and narrow in cross-section and of a width at least as wide as a moving sheet of metal to be inspected;
    each of said at least two lamps is positioned on said support means to direct its corresponding beam of light onto an inspection region through which such sheet of metal moves and where each such beam emitted from said at least two lamps is at a different angle of incidence relative to other such beams of light to provide at least two corresponding incident beams from a near dark field and a far dark field;
    means for controlling beam intensity of each of said lamps to permit independent adjustment of beam intensity of each of said at least two lamps;
    said inspecting means comprising means for sensing light reflected by a surface irregularity from at least one of said near dark field and said far dark field of said inspection region;
    said sensing means senses reflected light simultaneously from said at least two lamps while remaining at a single angle of reflection relative to normal for said inspection region;
    means for detecting sensed reflected light from said inspection region which is of an increased intensity greater than a predetermined minimum intensity or less than a predetermined maximum intensity, said detected reflected light of increased intensity or decreased intensity being indicative of an irregularity in surface quality of said moving sheet of metal; and
    means for recording location on such moving sheet of metal of a detected irregularity in surface finish quality.

2. Apparatus of claim 1 wherein said controlling means for beam intensity is adapted to adjust beam intensity of said far dark field lamp to a level greater than beam intensity of said near dark field lamp whereby surface irregularities are highlighted.

3. Apparatus of claim 1 wherein said sensing means is mounted on said supporting means by a adjustable mount, said adjustable mount being moveable to provide a variety of fixed positions which determines when said adjustable mount is fixed, said single angle of reflection.

4. Apparatus of claim 1 wherein said sensing means is a single video camera having an angle of view which is at least as wide as said inspection region.

5. Apparatus of claim 4 wherein said single video camera is a line scan video camera.

6. Apparatus of claim 1 wherein said at least two lamps direct respective beams of light in direction of travel of a sheet moving through said inspection region.

7. Apparatus of claim 6 wherein said single angle of reflection is approximately coincident with an angle of reflection corresponding to a specular angle of incidence for said inspection region.

8. Apparatus of claim 6 wherein said single angle of reflection is approximately coincident with an angle of reflection corresponding to such angle of incidence from said near dark field.

9. Apparatus of claim 6 wherein said single angle of reflection is approximately coincident with an angle of reflection corresponding to such angle of incidence from said far dark field.

10. Apparatus of claim 3 wherein said single angle of reflection ranges between 10° up to 45° relative to normal for said inspection region.

11. Apparatus of claim 10 wherein said lamp emitting a light beam from a near dark field is positioned on said supporting means at angle of incidence of at most 5° greater than or less than a specular angle of incidence which is defined by such single angle of reflection for said sensing means.

12. Apparatus of claim 10 wherein said lamp emitting a light beam from a far dark field is positioned on said supporting means at angle of incidence of less than 45° from a specular angle of incidence which is defined by such single angle of reflection for said sensing means.

13. Apparatus of claim 1 wherein a moving sheet of metal is passed over a roller, said at least two lamps direct their respective beams of light onto said inspection region defined by a finite narrow portion through which such moving sheet of metal passes as curved over said roller.

14. A method for inspecting surface finish quality of a moving sheet of metal comprising:
   moving said sheet of metal through an inspection region;
   illuminating a surface of said sheet of metal to be inspected with at least two incident beams of light from at least two corresponding lamps;
   orienting said lamps to direct said at least two beams of light having a plane of incidence along the direction of sheet motions;
   adapting each of said at least two lamps to emit a respective beam of light which is elongate and narrow in cross-section;
   positioning each of said at least two lamps to direct said at least two beams of light onto said inspection region at a different angle of incidence relative to each other to provide at least two corresponding incident beams from a near dark field and a far dark field;
   controlling beam intensity of each of said at least two lamps to permit independent adjustment of beam intensity of each of said at least two lamps;
   sensing simultaneously light reflected by a surface irregularity from incident light of said near dark field and said far dark field, said sensing of light being conducted at a single angle of reflection;
   detecting sensed reflected light from said inspection region which is of a increased intensity greater than a predetermined maximum intensity or of a decreased intensity less than a predetermined minimum intensity, setting said predetermined maximum or minimum intensity whereby reflected light of increased or decreased intensity indicates an irregularity in surface quality; and
   recording location on said moving sheet of metal of said detected irregularity in surface quality.

15. A method of claim 14 comprises:
   adjusting beam intensity from said far dark field to an level greater than beam intensity from said near dark field.

16. A method of claim 14 comprises sensing reflected light at various angles of reflection to enhance detection of various types of surface irregularities.

17. A method of claim 14 comprises positioning said lamp emitting said beam of light from said near dark field to define an angle of incidence at most 5° greater than or 5° less than said specular angle of incidence which is defined by said single angle of reflection.

18. A method of claim 14 comprises positioning said lamp emitting said beam of light from said far dark field to define an angle of incidence at least 45° from said specular angle of incidence which is defined by said single angle of reflection.

19. A method of claim 14 comprises passing said moving sheet over a roller, directing said at least two beams of light onto said inspection region to define a finite narrow inspection region through which said moving sheet passes as curved over said roller.

* * * * *